United States Patent [19]

Chiba et al.

[11] Patent Number: 4,465,624
[45] Date of Patent: Aug. 14, 1984

[54] PROCESS FOR PRODUCING ERYTHROPOIETIN

[75] Inventors: Hideo Chiba, Uji; Ryuzo Sasaki, Kyoto; Masatsugu Ueda, Kawagoe, all of Japan

[73] Assignee: Snow Brand Milk Products Co., Ltd., Higashi, Japan

[21] Appl. No.: 559,890

[22] Filed: Dec. 9, 1983

[30] Foreign Application Priority Data

Feb. 21, 1983 [JP]  Japan .................................. 58-26399

[51] Int. Cl.³ ...................... A61K 37/24; C07G 7/00
[52] U.S. Cl. .................................. 260/112 R; 424/85; 435/68; 435/172.2; 435/240; 435/241; 435/948; 935/109

[58] Field of Search ...................... 260/112 R; 424/85; 435/68, 172, 240, 241, 948

[56] References Cited

U.S. PATENT DOCUMENTS 3,865,801  2/1975  Chiba et al. ..................... 260/112 R
4,377,513  3/1983  Sugimoto et al. ............. 260/112 R Primary Examiner—Howard E. Schain
Attorney, Agent, or Firm—Oblon, Fisher, Spivak, McClelland & Maier

[57] ABSTRACT

Disclosed herein is a process for producing erythropoietin, comprising bringing a material containing erythropoietin into contact with an adsorbent having a monoclonal anti-erythropoietin antibody, adsorbing erythropoietin on the adsorbent, and eluting the absorbed erythropoietin from the adsorbent.

5 Claims, No Drawings

PROCESS FOR PRODUCING ERYTHROPOIETIN

The present invention relates to a process for producing a highly pure erythropoietin by effectively collecting erythropoietin from a material containing erythropoietin with an affinitychromatography in which an adsorbent having a monoclonal anti-erythropoietin antibody is used.

Erythropoietin (hereinafter referred to as EPO) has been known as an accelerating factor of erythrocyte-formation and EPO is a kind of hormones which acts on the erythrocytic stem cells in the bone marrow to accelerate the differentiation thereof into the erythrocytic cells. Although the chemical structure of EPO has not been completely elucidated, EPO itself is an acidic glycoprotein of a molecular weight of 30,000 to 40,000 produced predominantly in the kidney and can be applied broadly as a medicine for the anemic patients, the postoperative patients and the patients receiving homo-dialysis after kidney-extirpation.

Naturally, the formation of EPO in a living body is influenced by the balance between the demand and supply of oxygen in the living body and accordingly, the formation of EPO is accelerated when the living body is in a state of hypoxia and, to the contrary, the formation of EPO is reduced when the living body is in a state of hyperoxia. For instance, in an anemic patient, the formation of EPO is accelerated and as a result, EPO is excreted into his urine.

Hitherto, a process for isolating EPO with a stabilized activity from the human urine containing EPO has been known (referred to U.S. Pat. No. 3,865,801), wherein a solution of the crude EPO obtained from the human urine containing EPO in a phosphate-buffered saline solution is used as an original liquid, sodium p-aminosalicylate is added to the solution, the added solution is extracted with phenol, and the extract is dialyzed against the phosphate-buffered saline solution followed by collecting EPO from the dialyzate.

However, since the content of EPO in ordinary human urine is extremely low in the order of about 0.01 to 0.02% by weight of the whole protein in the urine, it is difficult to effectively produce EPO by the known process mentioned above and particularly, the process is not practical as a process for producing EPO as the medicine mentioned above. In this connection, EPO is produced only as a chemical reagent at present.

As a result of the present inventors' studies for effectively collecting EPO having a high purity from several materials containing EPO, the present inventors have succeeded in collecting EPO having a high purity effectively from the EPO-containing material by applying a column chromatography which uses an adsorbent having a monoclonal anti-EPO antibody, and have attained to the present invention.

The main object of the present invention is to provide a process for separating EPO effectively from a material containing EPO and obtaining the highly purified EPO preparation. The other objects of the present invention will be made clear from the following description.

The term "material containing EPO" mentioned herein means the urine of normal persons, the urine of the anemic patients, the crude urinary erythropoietin obtained therefrom, the supernatant liquid of the culture of the EPO-producing cells, the body fluid of an animal to which the EPO-producing cells have been transplanted, the extract fluid of the tissues of the transplanted animal and urine thereof.

In the present invention, the cases where the urine of the anemic patient was used as the material containing EPO are mainly explained as follows, however, it should be understood that the source of EPO according to the present invention is not limited thereto.

The characteristic feature of the present invention is a process for producing highly pure erythropoietin from a material containing erythropoietin, which comprises bringing said material containing erythropoietin into contact with an adsorbent having monoclonal anti-erythropoietin antibody, said monoclonal anti-erythropoietin antibody being prepared from hybridoma in which said hybridoma is obtained by cell-fusing a myeloma cell and a spleen cell of an experimental animal immunized by erythropoietin, adsorbing said erythropoietin on said monoclonal anti-erythropoietin antibody in said adsorbent, eluting said erythropoietin from said adsorbent, and collecting the eluted erythropoietin.

The monoclonal anti-erythropoietin antibody (hereinafter referred to as the monoclonal antibody) which is used to be bonded to the adsorbent in the present invention is produced from the hybridoma cells obtained by cell-fusing a cultured myeloma cell(s) and a cell(s) of the spleen of an experimental animal such as mouse or rat which has been immunized by administering EPO as an antigen which is collected from the urine such as an anemic patient's urine and purified the collected EPO. The cell fusion is preferably carried out between the cells of animal(s) of the same species. The cells of the spleen used herein (mainly B-cells) are obtained from the spleen of an experimental animal such as a mouse after about three days of the last immunization thereof used by intraperitoneal injection of an emulsion prepared by dissolving the purified EPO in an aqueous phosphate buffered saline solution (so-called PBS) and admixing Freund's adjuvant to the dissolved solution. In addition, on the occasion of immunization of the animal, it is preferable to repeat the injection at a regular interval, for instance, 2 weeks for promoting the immunization sufficiently.

The myeloma cell used in the present invention is a kind of malignant tumour cells and has a large multiplication rate. For instance, as the myeloma cells of mouse, the strains such as $P_3$-X63-Ag8, $P_3$-NSI/1-Ag 4-1, X 63-Ag 8 653 and the likes are used after cultivation to multiplicate.

The cell fusion of the cell(s) of the spleen and the cell(s) of myeloma may be carried out by the publicly known method as follows:

The tissue of the spleen is cut into minute pieces in a mixture of the serum of bovine fetus (hereinafter referred to as FCS) and RPMI 1640 synthetic culture medium (hereinafter referred to as RPMI 1640 medium) to which penicillin (100 U/ml), streptomycin (100 μg/ml), 2 mM of glutamine and 1 mM of pyruvic acid have been added, and is further separated or perfused into single cells. The obtained single cells are dispersed into the RPMI 1640 medium and the cells of the myeloma were admixed with the dispersion solution. After subjecting the mixture to centrifugation, the formed supernatant liquid is decanted and an aqueous 50% by weight of polyethylene glycol 1500 is added to the mixture of the cells as a fusion inducer to carry out the cell fusion.

In the next step, from the mixture of cells subjected to cell fusion, the hybridoma cells are selected out by the publicly known HAT-selection method. HAT-selection may be carried out by using a microtiter plate. For instance, the mixture of the cells subjected to cell-fusion are scattered onto a microtiter plate provided with 96 wells, and cultured in a HAT(hypoxanthine-aminopterin-thymidine) culture medium for about 2 weeks. After confirming the wells in which the cells subjected to cell fusion are proliferating without becoming extinct, the hybridoma cells are collected from such well.

The method for selecting the cells having a capability of producing the monoclonal anti-EPO antibody from the obtained hybridoma cells is described as follows:

After having examined and confirmed the activity of the hybridoma cells by solid phase method whether an antibody to EPO is produced, the examined hybridoma cells are transplanted into the abdominal cavity of a mouse to produce ascitic fluid in the mouse, and proteins are collected from the accumulated ascitic fluid by a publicly known method such as a fractionating method with ammonium sulfate. The collected proteins consist mainly of an immunoglobulin (IgG). The proteins mainly containing IgG as an antibody are made to be bonded to an adsorbent such as AFFI-GEL(made by Bio-Rad Co.) or SEPHADEX (made by Farmacia Co.) to obtain an adsorbent having antibody. The obtained adsorbent having antibody bonded thereon is packed into a column and then, by passing an authentic preparation of EPO through the prepared column and examining whether the prepared column has an ability of adsorbing EPO, it is inspected whether or not the obtained hybridoma cells have an ability of producing the anti-EPO antibody. Then, the hybridoma cells producing the anti-EPO antibody are subjected to monoclonization (monocloning) by the public known limiting dilution melhods, and the monoclonized hybridoma cells are examined on its stabilized productivity of the monoclonal antibody by the solid phase method and the adsorption method while utilizing the antibody-adsorbed column for examining the adsorbency of EPO. The necessary antibody can be supplied continuously at any time by melting the frozen cells, cultivating the cells and transplanting the cells into the abdominal cavity of a mouse since the obtained hybridoma cells can be preserved in a frozen state.

The monoclonal anti-EPO antibody produced by transplanting the monoclonized cells having an ability of producing the anti-EPO antibody, in the abdominal cavity of a mouse following the procedures mentioned above is purified and thereafter, the purified monoclonal anti-EPO antibody is bonded to an adsorbent such as AFFI-GEL or SEFADEX to prepare a specific adsorbent to which the antibody has been bonded. The specific adsorbent is used for adsorbing EPO from materials containing EPO to obtain EPO.

In the present invention, EPO is collected from materials containing EPO by an immuno-adsrobent chromatographic technique utilizing a column packed with the specific adsorbent to which the monoclonal anti-EPO antibody has been bonded as has been described above. As the material containing EPO, which is used as the starting material in the process according to the present invention, as has been mentioned before, of an anemic patient, urine of normal person, the supernatant liquid obtained from the cultured material of EPO-producing cells, body fluid of animal to which the EPO-producing cells have been transplanted, extract liquid of the tissues of the above-mentioned animal and the urine thereof may be mentioned other than the urine of an anemic patient.

On the occasion of treating one of these EPO-containing materials with the adsorbent to which the monoclonal anti-EPO antibody has been bonded, the urine such as an anemic patient's urine is filtered and the filtrate is condensed and subjected to desalting treatment or to SDS treatment and then, the treated specimen is applied onto the adsorbent of the column. In addition, for inactivating the protease in the urine, the urine may be treated with phenol or subjected to heating in advance of the application onto the adsorbent of the column.

The pretreated material containing EPO as mentioned above is passed through the column packed with the adsorbent to which the monoclonal anti-EPO antibody has been bound according to the present invention and as a result, the antibody selectively adsorbs EPO. Accordingly, it is not necessary to repeat the passing step and EPO adsorbed on the adsorbent is eluted by passing an eluting solution such as a mixture of aqueous 0.2M acetic acid solution and an aqueous 0.15M sodium chloride solution through the column and then, the eluate of EPO can be collected effectively and in a high purity.

After eluting EPO, the adsorbent in the column may be treated for regeneration and the regenerated adsorbent can be re-used for about 10 times. The treatment of the once used adsorbent for generation is carried out by passing a solution such as a mixed solution of acetic acid and an aqueous sodium chloride solution through the column packed with the adsorbent to be regenerated.

The purity of EPO obtained by the procedures mentioned above can be evaluated by measuring the EPO activity (unit) of the protein in the eluate. The EPO activity is measured by one of the publicly known methods such as the colony method by observing the erythrocytic colonies morphologically, the $^3$H-thymidine method by examining the take-up of $^3$H-thymidine into DNA of the colonies and the $^{59}$Fe method by examining the take-up rate of $^{59}$Fe to heme of the colonies. In addition, as the standard substance for measuring EPO, EPO(Erythropoietin Step 3, manufactured by Connort Co., Canada) prepared from the serum collected from an anemic sheep treated with phenylhydrazine may be used.

As has been described, according to the present invention, it is possible to effectively prepare EPO having a high purity from materials containing a very small amount of EPO. In addition, the antibody which has been bonded to the adsorbent used according to the present invention is the monoclonal antibody and accordingly, it is possible to obtain the antibody having the same property. Furthermore, since it is possible to obtain the antibody in a stable state, it may be said that the present invention is practical in preparing the purified erythropoietin.

The present invention will be explained more concretely while referring to the following nonlimitative examples.

EXAMPLE 1

(I) Preparation of monoclonal anti-EPO antibody (1) Preparation of EPO for use as an antigen for producing the monoclonal anti-EPO antibody:

Six hundred liters of urine collected from anemic patients were passed through an apparatus for ultrafiltration to remove low-molecular weight substances of up to 10,000 in molecular weight and then, the passed urine was condensed. The condensed urine was diluted with a suitable amount of water and the mixture was condensed in the same manner as above to carry out de-salting. Twenty liters of the obtained condensate of urine was subjected to freeze-drying to obtain 31.0 g of total protein in urine as a powder showing EPO activity of 1,800,000 Units/31.0 g(EPO activity was hereinafter determined by the protein-assay kit made by Bio-Rad Co.).

The obtained powder of total urine protein was purified by column-chromatography and SDS electrophoresis as shown below:

First stage column chromatography

The obtained powder of total urine protein was dissolved in a 5 mM tris-hydrochloric acid buffered solution(pH 6.8) and the solution of the powder was passed through a column packed with DEAE-cellulose (diethylaminoethylcellulose) which had been preliminarily equilibrated by the 5 mM tris-hydrochloric acid buffered solution(pH 6.8). The urine protein in the urine solution was adsorbed on the column and the adsorbed urine protein was eluted by a 5 mM tris-hydrochloric acid buffered solution containing 200 mM sodium chloride(pH 6.8) to obtain a fraction showing EPO activity. The fraction contained 16.0 g of protein and the specific activity of the fraction was 99 Units/mg protein.

Second stage column chromatography

The fraction showing EPO activity obtained in First stage was subjected to dialysis against water and the dialyzate was freeze-dried to obtain a powdery material. After dissolving the obtained powdery material in a buffered solution containing 10 mM of sodium phosphate(pH 6.8) and 4 M sodium chloride, the solution of the powdery material was passed through a column packed with PHENYLSepharose CL-4B which had been preliminarily equilibrated by a buffered solution (pH 6.8) containing 10 mM sodium phosphate and 4M sodium chloride to adsorb the protein thereon. The adsorbed protein was washed by a buffered solution (pH 7.1) containing 10 mM sodium phosphate and 0.5 M sodium chloride and then eluted by a mixture consisting of an aqueous 10 mM sodium hydroxide solution, an aqueous 20% ethylene glycol solution and an aqueous 6M guanidine hydrochloride solution to obtain a fraction showing EPO activity. The fraction contained 2.3 g of protein and the specific EPO activity of the fraction was 421 Units/mg protein.

Third stage column chromatography

The fraction showing EPO activity obtained in Second stage was subjected to dialysis against water and then, the powdery material was obtained from the dialyzate of the fraction by freeze-drying. The obtained powdery material was dissolved in 5 mM sodium phosphate-buffered solution (pH 6.9) and the solution of the powdery material was dialyzed against the same buffered solution. The obtained dialyzate was passed through a column packed with hydroxyapatite which had been equilibrated by 5 mM sodium phosphate-buffered solution (pH 6.9) to obtain an unadsorbed fraction. The obtained fraction contained 672 mg of protein and the specific EPO activity was 1,240 Units/mg protein.

Fourth stage column chromatography

The fraction showing EPO activity obtained in Third stage, that was the unadsorbed fraction, was dialyzed against water and the dialyzate was freeze-dried to obtain a powdery material. After dissolving the obtained powdery material in a buffered solution consisting of an aqueous 10 mM sodium phosphate solution (pH 6.9) and an aqueous 150 mM sodium chloride solution, the prepared solution was passed through a column packed with Sephadex G 100, which had been equilibrated by the same buffered solution as above, to carry out fractionation by the difference of molecular weight of the solutes and then, a fraction showing EPO activity was obtained. The amount of protein contained in the obtained fraction was 83 mg and the specific EPO activity of the fraction was 3,000 Units/mg protein.

Fifth stage column chromatography

After subjecting the fraction showing EPO activity obtained in Fourth stage to dialysis against water, the dialyzate was freeze-dried to obtain a powdery material. The obtained powdery material was dissolved in an aqueous 5 mM calcium chloride solution (pH 7.0), and the resultant solution was dialyzed against the same aqueous solution. The obtained dialyzate was adjusted to pH 4.5 with the addition of 0.1N hydrochloric acid solution and was passed through a column packed with SP-Sephadex which had been equilibrated by an aqueous 5 mM calcium chloride solution (pH 4.5). The material adsorbed onto the column was washed with a 5 mM calcium acetate-buffered solution (pH 4.5) and was eluted by a 20 mM calcium acetate buffered solution (pH 5.5) to obtain a fraction showing EPO activity. This fraction contained 16 mg of protein and showed the specific activity of EPO of 5,100 Units/mg protein.

Sixth stage column chromatography

After passing the fraction showing EPO activity obtained in Fifth stage through a column packed with Sephadex G 50 which had been equilibrated preliminarily by PBS, the column was eluted with the buffered solution to obtain a fraction showing EPO activity.

This fraction was passed through a column packed with the adsorbent to which the antibody had been bonded to carry out immuno-adsorbent chromatography thereby obtaining an unadsorbed fraction. The unadsorbed fraction contained 4 mg of protein and a specific EPO activity was 25,000 Unit/mg protein.

Preparation of the column packed with an adsorbent to which the antibody had been bound A mouse was immunized with the fraction showing EPO activity obtained by the column chromatography of Fifth stage. The cells of the spleen were obtained from the immunized mouse and the myeloma cells were obtained by a separate culture. The obtained cells of the spleen and the obtained myeloma cells were subjected to cell fusion to prepare hybridoma cells.

Antibodies were obtained from the prepared hybridoma cells and thereafter, the obtained antibodies were subjected to SDS electrophoresis.

As a result, an antibody to the protein showing a highly immunizing activity was selected, said protein being found in the lower molecular-side region adjacent to the region showing the EPO activity on the SDS gel electrophoresis. The selected antibody was bonded to a gel of AFFI-GEL(made by Bio-Rad Co.) and the gel having the antibody was packed into a column.

Purification of EPO by SDS electrophoresis

A fraction shwoing EPO activity (an unadsorbed fraction), which was obtained as above, was dialyzed against water and the dialyzate was freeze-dried to obtain a powdery material. The obtained powdery material was dissolved in a trishydrochloric acid-buffered solution containing 2% of SDS (pH 6.8). The prepared solution was subjected to 13% polyacrylamide gel-SDS electrophoresis following the ordinary procedures. The portion of the gel showing EPO activity was cut out. After adding PBS of three times as much as the obtained gel fraction to the thus obtained gel fraction, the resultant mixture was minutely ground down to extract a protein. The liquid extract contained 1.2 mg of protein and showed a specific EPO activity of 50,000 Units/mg protein. After subjecting the liquid extract to dialysis against water, the dialyzate was freeze-dried to obtain a powdery matter.

(2) Preparation of hybridoma cells: Collection of the cells of the spleen

A mouse (BALB/C mouse) was immunized by the following three-stage procedures while using the purified specimen of EPO obtained as above as an antigen.

First stage of immunization

A solution obtained by dissolving the purified specimen of EPO into PBS(an aqueous phosphate buffer saline solution) at a rate of 200 µg/ml was mixed with Freund's complete adjuvant to prepare an emulsion and 0.5 ml of the prepared emulsion corresponding to 50 µg of EPO protein was administered into the abdominal cavity of the mouse.

Second stage of immunization

A solution obtained by dissolving the purified specimen of EPO into PBS at a rate of 100 µg/ml was mixed with Freund's complete adjuvant to obtain an emulsion and 0.5 ml of the prepared emulsion corresponding to 25 µg of EPO protein was administered into the abdominal cavity of the mouse after two weeks of the first stage of immunization.

Third stage of immunization

After two weeks of the second stage of immunization, 0.5 ml of a solution obtained by dissolving the purified specimen of EPO into PBS at a rate of 50 µg/ml corresponding to 25 µg of EPO protein was further administered into the abdominal cavity of the treated mouse to complete the treatment of immunization.

After three days of the completion of immunication treatment, the spleen of the immunized mouse was aseptically extirpated. After washing the extirpated spleen with a mixture solution of a synthetic culture medium (RPMI 1640 solution) and an aqueous 15% bovine foetal serum solution (FCS), the washed spleen was cut into minute pieces in the same mixture solution with scissors to obtain mutually isolated single cells. After washing the obtained single cells two times with the same mixture solution, the washed single cells were dispersed in RPMI 1640 solution. The number of the cells therein was $2.0 \times 10^8$.

Preparation of myeloma cells

Myeloma cells ($P_3$-NSI/1-Ag 4-1) were cultured in the mixture of RPMI 1640 solution and FCS and the proliferated cells were washed with RPMI 1640 solution. The number of the cells was $10^8$.

Cell-fusion

After mixing the dispersion of the cells of the spleen obtained from the immunized mouse with the dispersion of the cultured mouse myeloma cells in RPMI 1640 solution, the mixture was subjected to centrifugation to remove the supernatant.

The obtained mixture of the two kinds of cells was subjected to cell-fusion in an aqueous 50% solution of polyethylene glycol 1500.

After mixing the fused cells obtained by the cell-fusion with a HT culture medium solution RPMI 1640 solution containing hypoxanthine, thymidine and an aqueous 15% solution of bovine fetal serum), the liquid mixture was scattered onto three microtiter plates each having 96 wells. The cells were cultured for two weeks in the respective walls on the plates while adding HAT culture medium(RPMI 1640 solution containing hypoxantine, aminopterin, thymidine and an aqueous 15% bovine foetal serum solution) from the second day on thereby effecting the selection by HAT. The proliferation of the hybridoma cells was confirmed in 264 wells.

(3) Selection of the cells with antibody-producing capability from the proliferated hybridoma cells:

From the proliferated hybridoma cells in the respective 264 wells(so-called 264 kinds of hybridoma cells), those cells producing an antibody which could be bound to the purified specimen of EPO were selected out while carrying out a screening by solid-phase method utilizing a biotin-avidin system. As a result, 19 kinds of cells were selected as the hybridoma cells suitable for producing antibody and particularly, seven kinds of cells in the 19 kinds thereof were confirmed to have a stabilized capability of producing the antibody.

(4) Selection of the cells producing the anti-EPO antibody by the examination of the capability of adsorbing EPO:

After preparing a column packed with an adsorbent to which an antibody produced by each of the 7 kinds of the cells had been bonded by the following procedures, the capability of the column in adsorbing EPO was examined to effect the further selection of the cells producing anti-EPO antibody.

Into the abdominal cavity of each of seven mice, $5 \times 10^6$ cells of each of the 7 kinds mentioned above were injected to produce the antibody and after collecting the ascitic fluid from the injected mouse, each of the ascites was fractioned by an aqueous 45%-saturated solution of ammonium sulfate and 40 to 60 mg of an Ig G fraction was obtained as the antibody, respectively. After bonding the obtained Ig G fraction to AFFI-GEL 10(made by Biorad Co.) by the following procedures, the prepared gel was packed in a column to obtain a column packed with AFFI-GEL 10 to which the antibody had been bonded.

The prepared AFFI-GEL 10 placed on a glass filter was washed with isopropyl alcohol under cooling with iced water and was further washed three times with iced water. The washed AFFI-GEL 10 was mixed at a volume ratio of 1:1 with a liquid containing the obtained antibody(Ig G fraction), 0.2M sodium hydrogen carbonate and 0.3M sodium chloride at pH 8.3. The resultant mixture was stirred for 5 hours at a temperature of 4° C. to effect the bonding of the antibody to AFFI-GEL 10. Then, the mixture was centrifuged to collect the antibody-bonded gel and after washing the collected gel with a mixture of an aqueous 0.1M sodium hydrogen carbonate solution and an aqueous 0.15M sodium chloride solution at twice, the washed gel was well mixed with an aqueous 0.1M ethanolamine hydrochloride solution (pH 8) for 60 min at room temperature to the antibody-bonded gel. The resultant mixture was packed in a column to prepare a column for adsorbing EPO. Each of the prepared seven columns corresponded to each of the seven kinds of the hybridoma cells mentioned above and the capability of each column in adsorbing EPO was examined by the following procedures while using the purified specimen of EPO obtained in the step (1).

After dissolving the purified specimen of EPO in PBS, the solution was passed through the column which had been prepared as above and preliminarily equilibrated with PBS and then the column was eluted by a mixture of an aqueous 0.2M acetic acid solution and an aqueous 0.15M sodium chloride solution. The EPO activity of both the non-adsorbed fraction and the eluate fraction was measured.

As a result, in the seven columns prepared as above, three columns showed the capability of adsorbing EPO.

(5) Cloning of the anti-EPO antibody-producing cells

Each of the three kinds of the anti-EPO antibody-producing hybridoma cells mentioned above was subjected to cloning the ordinary procedures of the limiting dilution method as follows.

After dispersing 50 cells of each kind of hybridoma and $10^8$ cells of the thymus of a BALB/C mouse in 4 weeks after birth in 10 ml of a mixture of RPMI 160 solution and an aqueous 15% solution of FCS, the dispersion was poured into 96 wells of a microtiter plate at a rate of 0.1 ml/well. The culture of the cells was carried out while adding the same mixture into each hole on the 5th and 12th day of the culture. The proliferated cells of hybridoma were screened on their capability of producing anti-EPO antibody by the same solid-phase method as above and further subjected to selection on the capability of producing anti-EPO antibody by examining the capability of adsorbing EPO thereof and then, the cloning was carried out.

As a result, the three strains E-1, E-2 and E-3 were obtained as the suitable strain of the hybridoma cells for the object of the present invention.

The production of the antibody was carried out in line with the procedure mentioned above while using each of the anti-EPO antibody-producing cell strains E-1, E-2 and E-3. Each of the cell strains was injected into the abdominal cavity of twenty mice to cause ascitic fluid and the total amount of ascitic fluid collected from the twenty mice was subjected to fractionation with the aqueous 45%-saturated solution of ammonium sulfate to obtain an Ig G fraction. As a result, 500 mg of the monoclonal antibody was obtained.

(II) Preparation of a column packed with an adsorbent to which the monoclonal antibody has been bonded By the same procedures mentioned above, each of the prepared Ig G fraction was bonded to AFFI-GEL 10 to obtain each 50 ml of a gel bonded to each monoclonal antibody in each monoclonal antibody producing cell strain and the obtained antibody-bonded gel was packed in a column to prepare a column for use in adsorbing EPO.

(III) Collection of EPO

By the same procedures as in (I), (1), 50 mg of the powdery total urine protein were obtained from an anemic patient and the powdery total urine protein showing an EPO activity of 2,900 Units was dissolved in 10 ml of PBS(phosphate-buffered saline solution). After subjecting the solution to dialysis for an overnight against 40 liters of PBS, the dialyzate was subjected to centrifugation to obtain 10 ml of the supernatant liquid which was used hereinafter as the original liquid.

After passing 20 ml of PBS through the column for adsorbing EPO, which was prepared by the same procedures as in (II) (0.8 cm in inside diameter and 4 cm in length, packed with AFFI-GEL 10 bonded to the monoclonal antibody produced by the cell strain E-1), at a rate of 20 ml/hour to equilibrate therewith 50 ml of a mixture of an aqueous 0.2M acetic acid solution and an aqueous 0.15M sodium chloride solution were passed through the column at a rate of 20 ml/hour to wash the column and further 20 ml of PBS was passed through the column to equilibrate therewith.

Through the preliminarily treated column, 10 ml of the original liquid prepared as above was passed at a rate of 5 ml/hour and after washing the adsorbed material in the column by the passing of 20 ml of PBS, then 20 ml of an aqueous 10 mM phosphoric acid-buffered solution containing 0.5M sodium chloride at 20 ml/hour and 20 ml of an aqueous 0.15M sodium chloride solution at a rate of 20 ml/hour in the above-mentioned order through the column, 20 ml of a mixture of an aqueous 0.2M acetic acid solution and an aqueous 0.15M sodium chloride solution was passed through the column at a rate of 5 ml/hour as an eluant to obtain an eluate containing highly pure EPO.

The EPO activity in the obtained eluate was 1,160 Units, that is, the recovery of 40% of the activity of the original liquid of 2,900 Units. In addition, the specific activity of EPO in the eluate was 45,000 Units/mg protein and the specific activity of EPO in the original liquid was 58 Units per mg protein and accordingly, the purity of EPO has been raised by the procedures to 780 times.

EXAMPLE 2

By using a column(0.8 cm in inside diameter and 4 cm in length, with a capacity of 2 ml) packed with a gel, to which the antibody produced by the hybridoma cell strain E-2 had been bonded, prepared by the same procedures as in Example 1, the following operation was carried out.

Into 10 ml of PBS containing 2% of SDS, 50 mg(showing EPO activity of 2,900 Units) of the powder of total urine protein collected from the anemic patient's urine by the same procedures as in Example 1 while using an ultrafiltration apparatus, was dissolved and after treating the solution by heating the resultant solution at 100° C. for 3 min, the treated solution was dialyzed for a night against 10 liters of PBS. After subjecting the dialyzate to centrifugation, the obtained supernatant liquid was diluted to five times in volume with PBS and the diluted liquid was passed through the column mentioned above, which had been pretreated as in Example 1, at a rate of 5 ml/hour. Then, after passing 20 ml of PBS, 20 ml of an aqueous 10 mM phosphoric acid-buffered solution containing 0.5M sodium chloride and 20 ml of an aqueous 0.15M sodium chloride solution in this order through the column to wash the adsorbed material in the column, 200 ml of a mixture of an aqueous 0.2M acetic acid solution and an aqueous 0.15M sodium chloride solution was passed through the column at a rate of 20 ml/hour as an eluant to obtain an eluate containing highly pure EPO. The EPO activity of the obtained eluate was 2,600 Units. Since the EPO activity of 2,900 Units of the original powder, the rate of collection was 90%. The specific activity of EPO in the eluate was 60,000 Units/mg protein. The original activity was 58 Units/mg protein of the original powder and accordingly, the purity of EPO was raised to as high as about 1,000 times of the original powder.

EXAMPLE 3

By using a column(2 cm in inside diameter and 6.4 cm in length, with a capacity of 20 ml) packed with a gel, to which the antibody produced by the hybridoma cell strain E-3 has been bonded, prepared by the same procedures as in Example 1, the following operation was carried out.

Five hundred mg of a powder of total urine protein collected from urine of an anemic patient (EPO activity of 29,000 Units) was dissolved in 50 ml of PBS containing 2% of SDS and the resultant solution was treated by heating thereof for 3 min at 100° C. The treated solution was dialyzed for an over-night against 40 liters of PBS and then was subjected to centrifugation to obtain 50 ml of a supernatant liquid.

After diluting the supernatant liquid to 5 times by volume with PBS, the diluted liquid was passed through the pretreated column at a rate of 20 ml/hour. After washing the column by passing 200 ml of PBS, 200 ml of an aqueous 10 mM phosphoric acid-buffered solution containing 0.5M sodium chloride and 200 ml of an aqueous 0.15M sodium chloride through the column in the above-mentioned order at a rate of 100 ml/hour, 200 ml of a mixture of an aqueous 0.2M acetic acid solution and an aqueous 0.15M sodium chloride solution was passed through the column to obtain an eluant containing highly pure EPO. The EPO activity in the EPO in the eluant was 25,000 Units and the recovering percentage of EPO was 86 based on the amount of 29,000 Units of EPO activity in the original powder. The specific EPO activity in the eluant was 60,000 Units/mg protein which showed the improvement of as large as about 1,000 in the purity of the purity of EPO.

What is claimed is:

1. A process for producing highly pure erythropoietin from a material containing erythropoietin, which comprises bringing said material containing erythropoietin into contact with an adsorbent having monoclonal anti-erythropoietin antibody, said monoclonal anti-erythropoietin antibody being prepared from hybridoma in which said hybridoma is obtained by cell-fusing a myeloma cell and a spleen cell of an experimental animal immunized by erythropoietin, adsorbing said erythropoietin on said monoclonal anti-erythropoietin antibody in said adsorbent, eluting said erythropoietin from said adsorbent, and collecting the eluted erythropoietin.

2. a process according to claim 1, in which the adsorbent is made from the monoclonal anti-erythropoietin antibody and Affi-Gel or Sephadex.

3. A process according to claim 1 or 2, in which the material containing erythropoietin is passed through a column packed with the adsorbent.

4. A process according to claim 1, in which the adsorbed erythropoietin is eluted with a mixture of acetic acid and an aqueous solution of sodium chloride.

5. A process according to claim 1, in which the once used adsorbent is regenerated and the regenerated adsorbent is repeatedly used in the adsorbing step.

* * * * *